(12) United States Patent
Courtade

(10) Patent No.: US 6,553,843 B1
(45) Date of Patent: Apr. 29, 2003

(54) TOOL TO BE FITTED ONTO A MACHINE FOR TRACTION TESTING OF TWO ELEMENTS WHICH ARE GLUED TO ONE ANOTHER

(75) Inventor: Frédéric Courtade, Castanet Tolosan (FR)

(73) Assignee: Centre National d'Etudes Spatiales (C.N.E.S.), Paris (FR)

( * ) Notice: Subject to any disclaimer, the term of this patent is extended or adjusted under 35 U.S.C. 154(b) by 0 days.

(21) Appl. No.: 09/701,021

(22) PCT Filed: May 26, 1999

(86) PCT No.: PCT/FR99/01233

§ 371 (c)(1),
(2), (4) Date: Nov. 22, 2000

(87) PCT Pub. No.: WO99/61884

PCT Pub. Date: Dec. 2, 1999

(30) Foreign Application Priority Data

May 28, 1998 (FR) .............................................. 98 06718

(51) Int. Cl.⁷ ................................................ G01N 3/22
(52) U.S. Cl. ....................................................... 73/827
(58) Field of Search .......................... 73/826, 827, 831, 73/832, 833, 837, 760

(56) References Cited

U.S. PATENT DOCUMENTS

| | | | | |
|---|---|---|---|---|
| 4,501,154 A | * | 2/1985 | Mori ............................ | 73/827 |
| 5,195,379 A | * | 3/1993 | Cussac et al. ................ | 73/859 |
| 5,259,174 A | * | 11/1993 | Fargeas et al. ............... | 73/833 |
| 5,313,841 A | | 5/1994 | Layher | |
| 5,337,614 A | | 8/1994 | Jiang et al. | |
| 6,199,433 B1 | * | 3/2001 | Beals, Jr. et al. ............. | 29/758 |

FOREIGN PATENT DOCUMENTS

| | | |
|---|---|---|
| DE | 37 23 475 | 1/1989 |
| GB | 620 183 | 3/1949 |

* cited by examiner

*Primary Examiner*—Max Noori
(74) *Attorney, Agent, or Firm*—Young & Thompson

(57) ABSTRACT

A tool to be fitted onto a machine for traction testing of two elements that are glued to one another at a gluing plane. The tool includes two assemblies, one of which includes a first part that is adjustably movable in a direction orthogonal to a traction axis after the tool is connected to the machine.

15 Claims, 3 Drawing Sheets

TOOL TO BE FITTED ONTO A MACHINE FOR TRACTION TESTING OF TWO ELEMENTS WHICH ARE GLUED TO ONE ANOTHER

BACKGROUND OF THE INVENTION

The invention relates to tooling to be fitted onto a machine for traction testing, by means of two traction units which are moved apart from one another according to a traction axis, of two elements which are glued to one another according to a gluing plane, such as a substrate made of semiconductor material (for example an integrated circuit chip) which is glued onto a base (for example a board of an integrated circuit case), each of these elements having a free surface which is parallel to the gluing plane.

In certain applications, it is necessary to be able to carry out a traction test which is designed to characterise the resistance of an assembly of two elements glued according to a gluing plane. Thus, for example, standard US MIL-STD 883 E defines the rules to be applied in order to carry out a test of this type, which is generally known as a STUD PULL TEST, in order to check the gluing of a substrate made of semiconductor material onto a base.

U.S. Pat. No. 5,313,841 describes tooling which makes it possible to carryout a test of this type, comprising for each element (substrate and base) a mechanism for assembly of this element to one of the two units of the machine for traction testing. Each mechanism for assembly comprises a block which has a surface which is glued to the free surface of the element before fitting onto the machine for traction takes place, and a connection end, which is introduced between the arms of a fork, and is connected by means of a detachable pivot connection to this fork, which in turn is connected to one of the traction units of the machine for traction testing.

This document states that one of the main problems which is encountered in order to be able to carry out these tests, is that of accuracy of alignment of the blocks, axially with one another, and perpendicularly to the gluing plane of the elements, during assembly of these blocks by being glued onto the elements, before fitting onto the machine takes place. In fact, if these alignments are not perfect, the test which is then carried out is not a true traction test, but a peeling test. U.S. Pat. No. 5,313,841 therefore recommends use of a specific assembly device, which is designed to improve the accuracy of gluing of each block to the corresponding element (substrate or base).

However, despite the use of an assembly device for gluing of the blocks, it is not always possible to obtain positioning which is always perfect, of the blocks. This means that the traction test cannot be carried out in normal conditions, since the breaking force obtained is far lower than that anticipated. This problem is exacerbated when the elements have certain shapes and/or dimensions which are particularly disadvantageous, in particular when they are elongate in a direction at right-angles to the traction axis.

SUMMARY OF THE INVENTION

The object of the invention is thus to eliminate these disadvantages, by proposing tooling which always makes it possible to carry out a true traction test, including with elements to be tested which have particularly disadvantageous shapes and/or dimensions, for example when at least one of the elements is elongate in a main longitudinal direction which is parallel to the gluing plane, and/or when the gluing plane has a longer length, according to a main longitudinal direction of this type.

The object of the invention is also to provide tooling of this type which is simple to produce, and assures the reproducibility of the results of the tests carried out.

For this purpose, the invention relates to tooling to be fitted onto a machine for traction testing, with traction units which are moved apart from one another according to a traction axis, of two elements which are glued to one another according to a gluing plane, each of these elements having a flat free surface which is parallel to the gluing plane, this tooling comprising, for each element, a mechanism for assembly of this element to one of the two traction units of the machine, this mechanism for assembly being designed such that the gluing plane can be disposed perpendicularly to the traction axis, and comprising a first part which is designed such that it can be glued, before fitting onto the machine takes place, onto a free surface of the element parallel to the gluing plane, wherein the mechanism for assembly of at least one of the two elements is designed, after fitting onto the machine has taken place, to permit modification of the position of the said first part relative to the corresponding traction unit, according to at least one direction, the so-called direction of adjustment, at right-angles to the traction axis.

Thus, contrary to the prior art, in which it was attempted to provide an assembly which was as accurate as possible, before fitting it onto the machine, without any possibility of further modification of the relative positions of the tooling blocks and the elements, the inventor has found that, on the contrary, it is possible and preferable to provide regulation of alignment after fitting onto the machine has taken place. The accuracy of assembly of the tooling parts to the elements to be tested is then less important. On the other hand, the tooling according to the invention then permits accurate alignment, by regulation according to the direction of adjustment, of the position of the elements relative to the traction axis, after fitting onto the machine has taken place, and thus immediately before the traction test is carried out.

Preferably, advantageously and according to the invention, each of the two mechanisms for assembly is designed, after fitting onto the machine has taken place, to permit modification of the position of the said first part, relative to the corresponding traction unit, according to at least one direction of adjustment at right-angles to the traction axis.

The tooling according to the invention is advantageously applicable for fitting, onto a machine for traction testing, of two elements which are glued to one another, according to a gluing plane which has at least one portion which is elongate according to at least a single main longitudinal direction (for example in the form of a rectangular strip), and which in particular, in this direction, has a length which is more than five times longer than its width, for example approximately ten to fifty times its width. In this case, advantageously and according to the invention, at least one of the two mechanisms for assembly is designed to have a direction of adjustment parallel to this main longitudinal direction.

In addition, advantageously and according to the invention, each of the two mechanisms for assembly is designed to have a single direction of adjustment.

In addition, advantageously and according to the invention, the two mechanisms for assembly are designed such that at least one direction of adjustment of one of the two mechanisms for assembly is parallel to a direction of adjustment of the other mechanism for assembly. If the gluing plane is elongate in the main longitudinal direction, the directions of adjustment of the two mechanisms for assembly are parallel to the main longitudinal direction.

As a variant or in combination, advantageously and according to the invention, the two mechanisms for assembly are designed such that at least one direction of adjustment of one of these two mechanisms for assembly is at least substantially perpendicular to one direction of adjustment of the other mechanism for assembly. This variant is advantageously applicable when the gluing plane is not significantly elongate in one direction (for example when it is generally in the shape of a square or disk).

According to another advantageous characteristic of the invention, at least one of the two mechanisms for assembly, and advantageously each of the two mechanisms for assembly, which are similar, comprises:

a first part, which is designed to be able to be glued onto a free surface of the corresponding element, parallel to the gluing plane;

a second part, which is designed to be able to be secured axially to the corresponding traction unit of the machine; and means for axial securing of the first part and of the second part, which are designed to permit relative displacements of these first and second parts in translation, according to at least one direction of adjustment in translation, parallel to the gluing plane.

"Axial securing" means for the two parts, mean any means which are designed to render the two parts integral in the axial direction of traction, such that the traction forces generated by the machine are transmitted integrally between these two parts, and to the corresponding element.

When the two mechanisms for assembly are similar, the tooling according to the invention thus comprises two pairs of parts, one for assembly of the first element to a first traction unit of the machine, and the other for assembly of the second element to the second traction unit of the machine.

Advantageously and according to the invention, the mechanisms for assembly are designed such that, after each of the first parts has been glued to the corresponding element, the two directions of adjustment in translation are parallel to one another.

Advantageously and according to the invention, the means for axial securing of the first part and of the second part are formed by a sliding assembly of the first and the second parts, one on the other, which permits relative displacements of these two parts in translation according to the direction of adjustment in translation. Advantageously and according to the invention, the sliding assembly is of the dovetail type. Any other equivalent form of sliding assembly can be used. In order to provide axial securing which permits adjustment in translation parallel to the gluing plane, the sliding assembly can be formed from two assembly portions, each of which belongs respectively to one of the two parts, in contact with one another according to a contact surface which is a regulated generatrix surface, which defines the direction of adjustment in translation, and has at least one transverse return of an assembly portion, around the other assembly portion, such as to lock the two parts perpendicularly to the direction of adjustment in translation, i.e. according to the axial direction of traction. In the case of a dovetail, the said contact surface is a regulated surface with a trapezoidal cross-section.

In addition, advantageously and according to the invention, the second part is designed to be able to be secured axially to the corresponding traction unit of the machine, by means for attachment which comprise at least one pivot connection, with a swivel pin which is at right-angles to the traction axis, and the direction of adjustment in translation is at right-angles to this swivel pin. Advantageously and according to the invention, the means for attachment of the second part to the corresponding traction unit of the machine comprise a ball connection. The said means for attachment are also designed to secure the second part axially to the traction unit.

It should be noted that the second part is connected firstly to a traction unit, and secondly to the first part. This second part therefore does not need to be modified according to the shapes and/or dimensions of the element of which it permits assembly. On the other hand, the first part is designed according to the shapes and/or dimensions of the flat free surface of the element to which it is designed to be glued. The first part thus has a flat gluing surface which is designed to be able to be placed in contact with the flat free surface of the element, and to be glued to the latter. This gluing surface has an area which is larger than, or equivalent to, sixty per cent of the area of the gluing plane, and can advantageously be larger than the area of the gluing plane.

The invention is more particularly and advantageously applicable to the case in which the elements consist of a substrate, such as a chip made of semiconductor material (integrated circuit), with a shape which is elongate according to a longitudinal direction, and in particular has a length of between 1 cm and 20 cm, for a width of between 0.5 mm and 5 cm, glued onto a base which also has an elongate shape according to the longitudinal direction. The tooling is then characterised in that the two mechanisms for assembly have a direction of adjustment parallel to the longitudinal direction of the substrate.

The invention also relates to tooling characterised in combination by all or some of the characteristics described previously or hereinafter.

BRIEF DESCRIPTION OF THE DRAWINGS

Other objects, characteristics and advantages of the invention will become apparent from reading the following description, provided with reference to the attached figures, in which.

DESCRIPTION OF THE PREFERRED EMBODIMENTS

Figure 1:
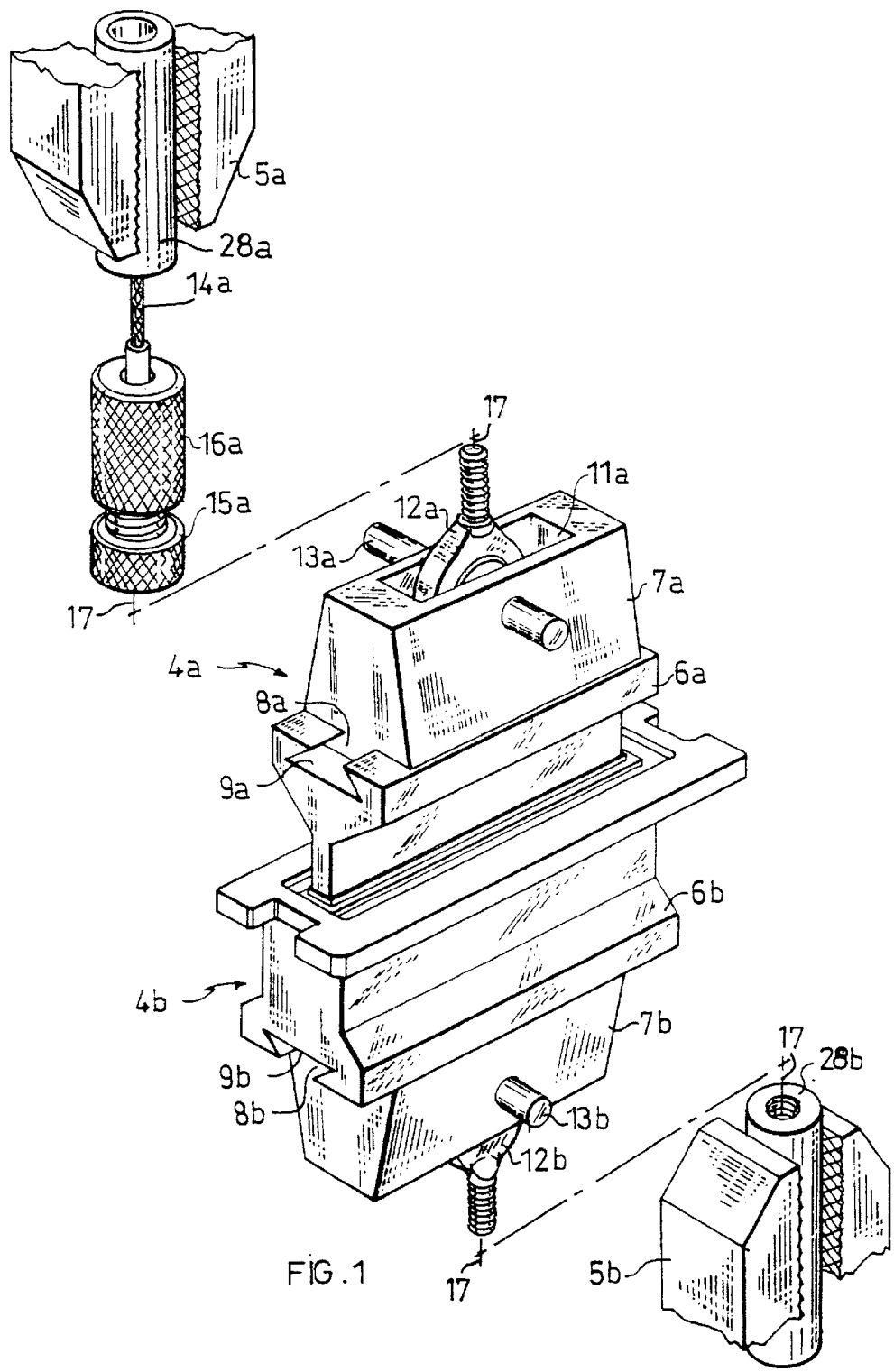
FIG. 1 is a schematic perspective view of tooling according to the invention, for fitting of a elongate chip made of semiconductor material glued onto a base.
Figure 2:
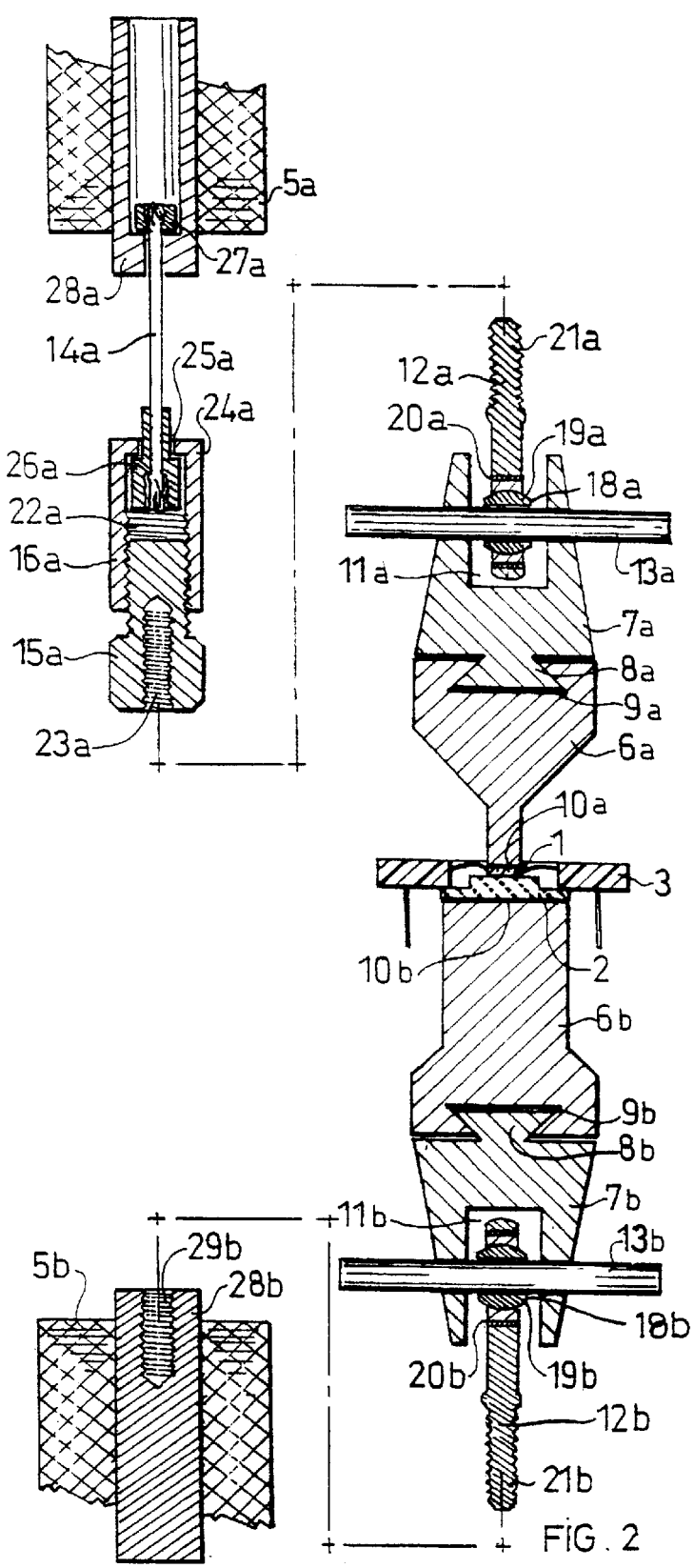
FIG. 2 is a schematic view in axial cross-section, perpendicularly to the longitudinal direction of the chip, of the tooling in FIG. 1.
Figure 3:
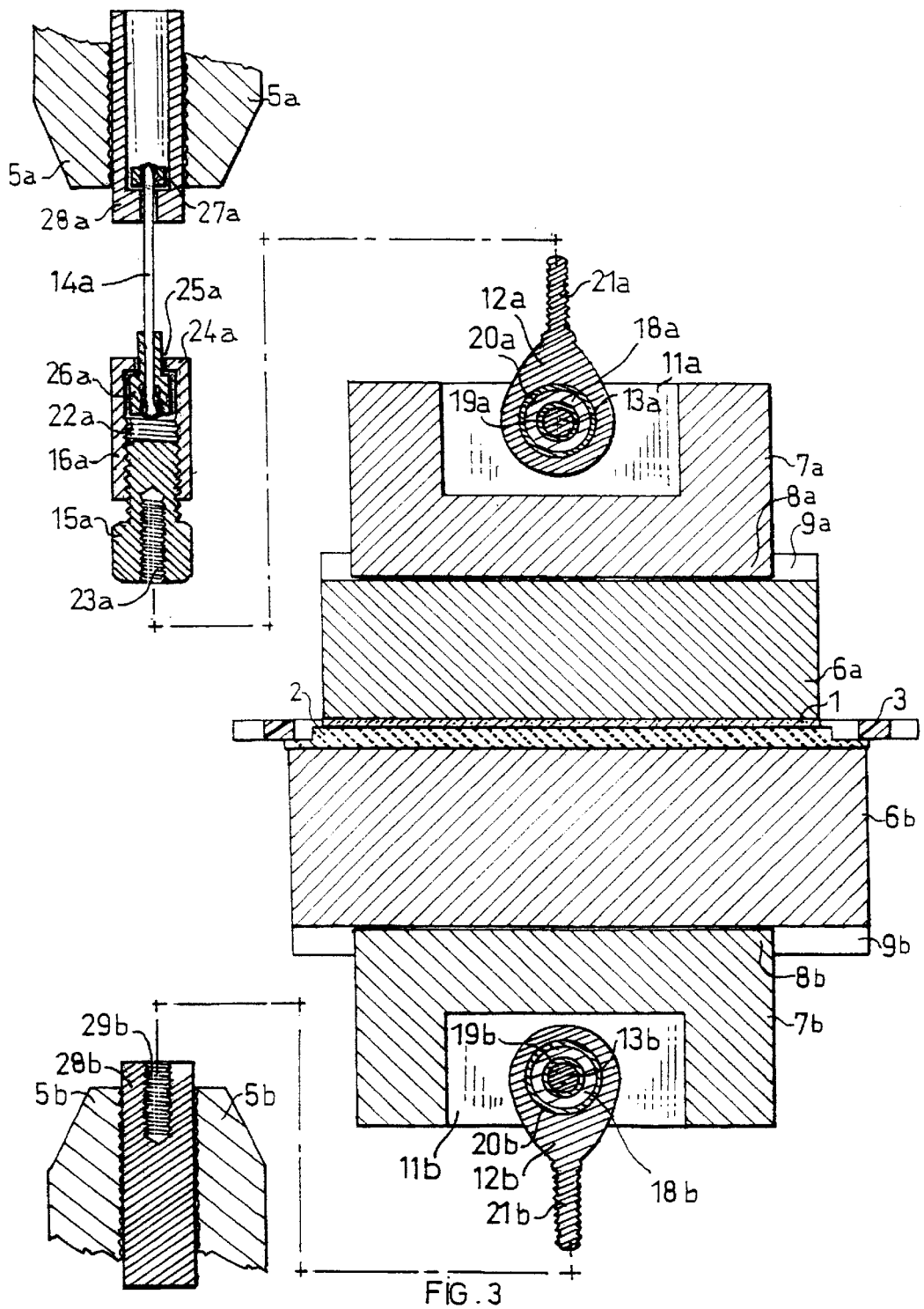
FIG. 3 is a schematic view in axial cross-section, parallel to the longitudinal direction of the chip, of the tooling in FIG. 1.

The tooling according to the invention shown in the figures makes it possible to subject to a traction test, perpendicularly to the gluing plane, a substrate 1 such as a chip made of semiconductor material with an elongate shape, glued to a base 2, the assembly being associated with a case 3, in a conventional manner. In fact, substrates or electronic chips made of semiconductor material (integrated circuit) are sometimes incorporated in systems in which it is necessary to assure excellent mechanical hold of the substrate relative to its base. This is the case in particular for spatial systems, for example chips which constitute strips which act as image sensors. In these applications, the mechanical hold of the chip is assured by gluing the latter onto its base according to a gluing plane which corresponds to the surface of contact of the chip with its base. The gluing plane has a highly elongate globally rectangular shape. Conventionally, the gluing plane is elongate according to a main longitudinal direction, with a length which is approximately 1 to 20 cm, and in general, in particular, is between 5 cm and 15 cm, for a width of between 0.5 mm and 5 mm, and in general, in particular, between 1 and 5 mm. The substrate or chip 1 and the base 2 are two elements 1, 2 which are glued to one another according to a gluing plane, and each have a free surface parallel to the gluing plane.

The tooling according to the invention comprises a first mechanism 4a for assembly of the chip 1 to one 5a of the traction units of the machine, and a second mechanism 4b for assembly of the base 2 to the other traction unit 5b of the machine. Throughout the text, the reference "a" designates units which constitute the first mechanism 4a for assembly of the chip 1 to the first traction unit 5a, and the reference "b" designates the similar units of the second mechanism 4b for assembly of the base 2 to the second traction unit 5b. The traction units 5a, 5b can for example be chucks or clamping jaws of the machine. They define a traction axis 17 which is represented by broken lines in the figures, for the purposes of illustration. During the test, the two traction units 5a, 5b are moved apart from one another in translation according to this traction axis 17.

The two mechanisms 4a, 4b for assembly are similar, and each of them comprises a first part 6a, 6b, which is designed to be able to be glued respectively onto a free surface of the chip 1 or of the base 2, which is parallel to the gluing plane of the chip 1 onto the base 2, and a second part 7a, 7b, which is designed to be able to be connected firstly to the first part 6a, 6b, and secondly to the corresponding traction unit 5a, 5b of the machine. Each mechanism 4a, 4b for assembly additionally comprises means 8a, 8b, 9a, 9b for axial securing of the first part 6a, 6b and of the second part 7a, 7b, such that these two parts 6a, 6b, 7a, 7b are integral with one another axially, according to the axial direction of traction, the traction forces being transmitted from each traction unit 5a, 5b respectively to the chip 1 or to the base 2, by the pair of parts 6a, 6b, 7a, 7b.

The means 8a, 8b, 9a, 9b for axial securing of these two parts are designed to permit relative displacements of the first part 6a, 6b and of the second part 7a, 7b relative to one another in translation, according to at least one direction of adjustment in translation which is parallel to the gluing plane of the chip 1 onto the base 2. For this purpose, the first part 6a, 6b comprises a dovetail groove 8a, 8b, which is designed to be able to be engaged and slide in a dovetail recess 9a, 9b in the second part 7a, 7b. Thus, the means for securing are formed by a sliding assembly of the dovetail type, the first part 6a, 6b and the second part 7a, 7b being able to slide relative to one another according to a direction of adjustment in translation. As can be seen, the direction of adjustment permitted by the sliding dovetail assembly 8a, 9a of the first mechanism 4a for assembly is parallel to the direction of adjustment permitted by the sliding dovetail assembly 8b, 9b of the second mechanism for assembly 4b, and these directions of adjustment are parallel to the main longitudinal direction of the chip 1 and of the base 2.

The first part 6a, 6b has a rectangular surface, respectively 10a, 10b, for gluing respectively onto the chip 1 or onto the base 2, and this gluing surface 10a, 10b has dimensions which correspond exactly to those of the free surface of the chip or of the base 2, opposite and parallel to the gluing plane onto which it must be glued.

The first part 6a, 6b is glued respectively onto the chip 1 or onto the base 2, by means of a glue which provides an assembly which is reliable and strong when subjected to traction. It will be appreciated that the strength of this gluing must be greater than that of the gluing of the chip 1 to its base 2. A cyanoacrylate glue or any other equivalent glue can be used.

The second part 7a, 7b has a recess 11a, 11b, which is designed to receive an attachment part 12a, 12b. The second part 7a, 7b and the attachment part 12a, 12b both have transverse apertures, such that they can be assembled by a transverse pin 13a, 13b, which forms a pivot connection with a swivel pin at right-angles to the traction axis 17 of the machine for traction testing. Rotation of the second part 7a, 7b relative to the attachment part 12a, 12b around the axis of the pin 13a, 13b is possible.

The attachment part 12a, 12b comprises a bearing 18a, 18b, which forms a ball connection, containing an inner cage 19a, 19b which is provided with an aperture in order to receive the pin 13a, 13b, and has a spherical outer shape, which is fitted such as to rotate freely in an outer cage 20a, 20b, which is integral with the attachment part 12a, 12b. The attachment part 12a, 12b is extended axially by a threaded end portion 21a, 21b.

Advantageously and according to the invention, between the second part 7a and the traction unit 5a, at least one of the mechanisms 4a, 4b for assembly comprises a cable 14a, which is resiliently flexible, is not extendable axially, and for example is made of steel. In addition, at least one 4a of the mechanisms 4a, 4b for assembly comprises a tension device 15a, 16a.

In the embodiment shown, only one 4a of the mechanisms for assembly comprises a cable 14a and a tension device 15a, 16a. The two mechanisms 4a, 4b for assembly can also be identical, and can each comprise a cable and a tension device.

The tension device 15a, 16a comprises a threaded part 15a, which is designed to be able to be engaged in a female thread 22a in a tapped part 16a. The threaded part 15a comprises a female thread 23a which receives the threaded end portion 21a of the attachment part 12a. The tapped part 16a has a base 24a which is provided with an aperture 25a for passage of the cable 14a, one end of which supports a stop 26a, which abuts the base 24a axially. The other end of the cable 14a supports a stop 27a or a cable clamp, for axial securing to a cylinder 28a which is clamped in the clamping jaws 5a of the traction machine.

When the threaded part 15a is rotated relative to the tapped part 16a, the cable 14a is tightened or relaxed.

The other mechanism 14b for assembly also comprises an attachment part 12b, which is associated with the second part 7b by means of the pin 13b and the bearing 18b, forming a ball connection. The threaded end portion 21b of the attachment part is engaged in a female thread 29b in a cylinder 28b, which is clamped in the clamping jaws 5b of the traction machine. In a variant, not shown, the attachment part 12b can comprise an cylindrical extension, which is clamped directly in the clamping jaws 5b.

In order to install the tooling according to the invention in a machine for traction testing, the procedure is as follows. Firstly, the first part 6b is glued onto the free surface of the base 2, then the first part 6a is glued onto the free surface of the chip or substrate 1. The attachment parts 12a, 12b are assembled to each of the corresponding traction units 5a, 5b (clamping jaws), by means of the cable(s) 14a and the tension device(s), as applicable, and the clamping jaws 5a, 5b are clamped onto the cylinders 28a, 28b. The second parts 7a, 7b are then assembled respectively onto the first parts 6a, 6b, which are glued respectively to the chip 1 and onto the base 2, by engaging the grooves 8a, 8b of the dovetails in the corresponding recesses 9a, 9b. The second parts 7a, 7b are then assembled to the attachment parts 12a, 12b, by means of the pins 13a, 13b, one after another, the cable(s) 14a being previously relaxed. The cables(s) 14a is/are tightened by acting on the tension device(s) 15a, 16a. Each groove 8a, 8b is slid in each recess 9a, 9b, such that the two mechanisms 4a, 4b for assembly thus constituted are perfectly aligned according to the axial direction (traction axis 17) of the traction units 5a, 5b. The actual traction test can then be carried out in optimal conditions.

The tests carried out have shown that it has been possible to apply forces of more than 300 kgf (2,943 N), in order to detach chips 8 cm long and 2 mm wide, according to their gluing plane.

What is claimed is:

1. A tool for testing adhesion of two elements to each other in a device in which the two elements are pulled apart by two traction units along a traction axis that is perpendicular to a gluing plane along which the two elements are adhered to each other, the tool comprising:

two assemblies, each of said assemblies having a first part that is arranged and adapted to be adhered to a surface of a respective one of the two elements that is parallel to the gluing plane, each of said assemblies being arranged and adapted to be connected to a respective one of the traction units to be pulled in a respective direction along the traction axis, wherein said first part of at least one of said assemblies is adjustably movable relative to the respective one of the traction units in a direction orthogonal to the traction axis after the tool is connected to the traction units.

2. The tool of claim 1, wherein said first part of the at least one said assembly is adjustably movable in a direction perpendicular to the traction axis.

3. The tool of claim 1, wherein the gluing plane has a longitudinal axis and said first part of the at least one said assembly is adjustably movable in a direction parallel to this longitudinal axis.

4. The tool of claim 1, wherein said first part of the at least one said assembly is adjustably movable relative to the respective one of the traction units only in the direction orthogonal to the traction axis.

5. The tool of claim 1, wherein said first parts of both of said two assemblies are adjustably movable relative to the respective one of said traction units in a direction orthogonal to the traction axis after the tool is connected to the traction units.

6. The tool of claim 5, wherein both said first parts are adjustably movable in directions that are parallel to each other.

7. The tool of claim 5, wherein both said first part are adjustably movable in directions that are perpendicular to each other.

8. A tool for testing adhesion of two elements to each other in a device in which the two elements are pulled apart by two traction units along a traction axis that is perpendicular to a gluing plane along which the two elements are adhered to each other, the tool comprising:

two assemblies, each of said assemblies having a first part that is arranged and adapted to be adhered to a surface of a respective one of the two elements that is parallel to the gluing plane, each of said assemblies being arranged and adapted to be connected to a respective one of the traction units to be pulled in a respective direction along the traction axis, wherein said first part of at least one of said assemblies is linearly movable relative to the respective one of the traction units in a plane generally parallel to the gluing plane after the tool is connected to the traction units.

9. The tool of claim 8, wherein the gluing plane has a longitudinal axis and said first part of the at least one said assembly is movable in a direction parallel to this longitudinal axis.

10. The tool of claim 8, wherein said first parts of both of said two assemblies are movable relative to the respective one of said traction units in respective planes that are generally parallel to the gluing plane after the tool is connected to the traction units.

11. A tool for testing adhesion of two elements to each other in a device in which the two elements are pulled apart by two traction units along a traction axis that is perpendicular to a gluing plane along which the two elements are adhered to each other, the tool comprising:

two assemblies, each of said assemblies having a first part that is arranged and adapted to be adhered to a surface of a respective one of the two elements that is parallel to the gluing plane, and a second part that is axially secured to said first unit and is arranged and adapted to be connected to a respective one of the traction units, wherein said first and second parts of at least one of said assemblies are adjustably movable relative to each other in translation in a direction generally parallel to the gluing plane after the tool is connected to the traction units.

12. The tool of claim 11, wherein said first and second parts of both of said assemblies are adjustably movable relative to each other in translation in a direction generally parallel to the gluing plane after the tool is connected to the traction units.

13. The tool of claim 11, wherein said first and second parts of the at least one of said assemblies comprise corresponding sliding parts so that said first and second parts slide relative to each other.

14. The tool of claim 13, wherein said sliding parts comprise dovetailed parts.

15. The tool of claim 11, wherein said second part comprises a swivel pin that is arranged and adapted for connection to the respective one of the traction units, said swivel pin being generally perpendicular to the traction axis.

* * * * *